United States Patent
Gueremy et al.

[11] 3,987,042
[45] Oct. 19, 1976

[54] PHENOTHIAZINE DERIVATIVE

[76] Inventors: Claude Gueremy, 3, rue Daumesnil, Houilles; Robert Labey, 75, avenue G. Clemenceau, Le Vesinet; Didier Wirth, 2 bis, rue Verhaeren, St. Cloud; Maurice Auclair, 12, rue Andre Theuriet, Bourg La Reine, all of France

[22] Filed: Oct. 10, 1975

[21] Appl. No.: 621,617

Related U.S. Application Data

[63] Continuation of Ser. No. 389,376, Aug. 17, 1973, abandoned, which is a continuation of Ser. No. 15,950, March 2, 1970, abandoned.

[30] Foreign Application Priority Data

Mar. 3, 1969 United Kingdom............... 11249/69

[52] U.S. Cl............................. 260/243 A; 424/247
[51] Int. Cl.².................................... C07D 453/02
[58] Field of Search............................. 260/243

[56] References Cited
UNITED STATES PATENTS

| | | | |
|---|---|---|---|
| 2,945,855 | 7/1960 | Feldkamp et al.......... | 260/243 |
| 3,140,284 | 7/1964 | Habicht et al............ | 260/243 |
| 3,360,526 | 12/1967 | Minor..................... | 260/294.7 |
| 3,370,058 | 2/1968 | Judd et al................ | 260/239 |

*Primary Examiner*—Harry I. Moatz
*Attorney, Agent, or Firm*—Haseltine, Lake & Waters

[57] ABSTRACT

Phenothiazine derivatives are described of the formula

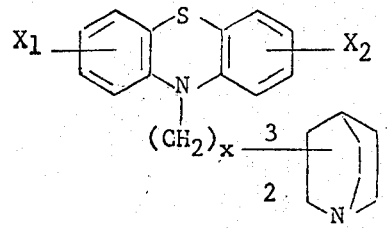

in which $X_1$ and $X_2$, which may be the same or different, are H, R, F, Cl, Br, OR, CN, —COR, CH₃, —S—R, —SOR, —SO₂R or —SO₂N(CH₃)₂, where R is an alkyl group having from 1 to 4 carbon atoms, and the quinuclidine ring is substituted by the group —(CH₂)ₓ— in the 2- or 3- position, $x$ being 1 or 2 when said group is substituted in the 2-position and being 0 or 1 when said group is substituted in the 3-position (because of electronic hindrance), and their acid addition and quaternary ammonium salts, have valuable pharmacological properties. In particular, these compounds have anti-histaminic, anti-cholinergic, adrenolytic, neuro-sedative, tranquillizing and/or spasmolytic properties.

These compounds are prepared by condensing an appropriate phenothiazine with a quinuclidine derivative of the formula

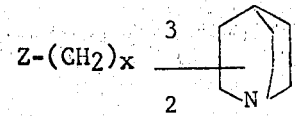

in which $x$ has the above-stated meaning and Z is a halogen atom or a reactive ester group.

1 Claim, No Drawings

PHENOTHIAZINE DERIVATIVE

CROSS RELATED APPLICATION

This application is a continuation of copending application Ser. No. 389,376 filed Aug. 17, 1973 and now abandoned which in turn is a continuation of application Ser. No. 15,950, filed Mar. 2, 1970 and now abandoned, which claims the priority of our application filed in Great Britain on Mar. 3, 1969.

The present invention is concerned with phenothiazine derivatives, their preparation and compositions containing them.

We have found that phenothiazine derivatives of the formula

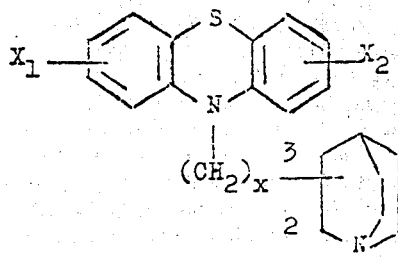

in which $X_1$ and $X_2$, which may be the same or different, are H, R, F, Cl, Br, OR, CN, —COR, $CF_3$, —S—R, —SOR, —$SO_2$R or —$SO_2N(CH_3)_2$, where R is an alkyl group having from 1 to 4 carbon atoms, and the quinuclidine ring is substituted by the group —$(CH_2)_x$— in the 2- or 3-position, $x$ being 1 or 2 when said group is substituted in the 2 positions and being 0 or 1 when said group is substituted in the 3-position (because of electronic hindrance), and their acid addition and quaternary ammonium salts, have valuable pharmacological properties. In particular, these compounds have antihistaminic, anti-cholinergic, adrenolytio, neurosedative, tranquillising, and/or spasmolytic properties.

The compounds of formula I can, for greater clarity, be expressed also by the following formula:

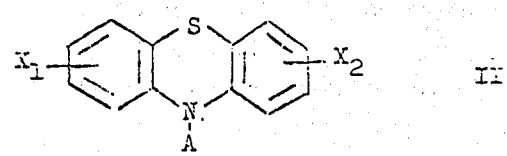

in which $X_1$ and $X_2$ have the above-stated meanings and A is

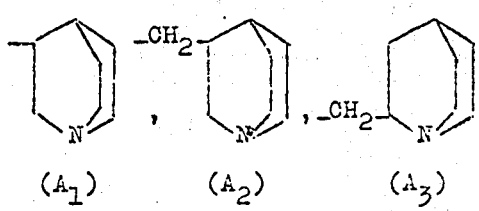

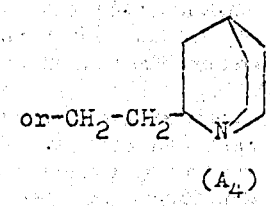

The compounds of formula I (and formula II) and their acid addition and quaternary ammonium salts, are novel and constitute one aspect of the present invention.

The present invention also comprises pharmaceutical compositions comprising one or more of these novel compounds and an inert, physiologically-acceptable carrier.

These compounds can be prepared by condensing a phenothiazine derivative of the formula

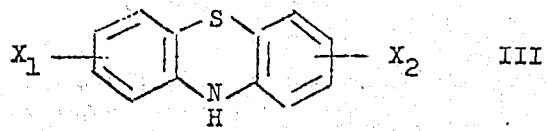

in which $X_1$ and $X_2$ have the above-stated meanings, with a quinuclidine derivative of the formula

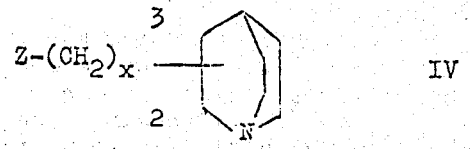

in which x has the above-stated meaning and Z is a halogen atom or a reactive ester group, for example an arylsulphonyloxy or alkylsulphonyloxy group. The reaction can be carried out without solvent under an inert atmosphere, but it is generally preferred to effect the reaction in the presence of a suitable inert non-polar or polar organic solvent, such as toluene, xylene, dimethylformamide or hexamethylphosphotriamide, or a mixture of two or more thereof, advantageously under reflux. The condensation can be effected without a condensation agent, but it is preferred to use a basic condensation agent, such as an alkali metal or a derivative thereof, for example an alkali metal hydride, amide or hydroxide, or a suitable organometallic derivative of an alkali metal.

The phenothiazine derivatives of formula III can be prepared by known procedures which are described in the chemical literature.

The quinuclidine derivatives of formula IV can be prepared from the corresponding alcohols (IV, Z = OH) by the use of any of the known processes for replacing a hydroxyl group by a halogen or a reactive ester group. In particular in the case where the halogen is iodine, the halide can be prepared in situ by the addition of a trace of alkali metal iodide to the reaction mixture containing the corresponding chloride or arylsulphonate. The alcohols (IV, Z = OH) are four in number and can be prepared by the processes described below:

i. 3-Quinuclidinol can be prepared by the reduction of 3-quinuclidinone, in particular by catalytic reduction as described by Grob and coll, Helv. Chim. Acta, 40, (1957), 2170.

ii. 3-Hydroxymethyl-quinuclidine can be prepared by the reduction of an ester of 3-carboxy-quinuclidine, in particular 3-methoxycarbonyl-quinuclidine, with lithium aluminum hydride as described by Grob and coll., Helv. Chim. Acta, 37 (1954), 1689.

iii. 2-Hydroxymethyl-quinuclidine can be prepared by the reduction of an ester of 2-carboxy-quinuclidine with lithium aluminium hydride or by the reduction of 2-ethoxycabonyl-quinuclidine with sodium in ethanol as described by Prelog and coll., *Annalen*, 545 (1940), 259.

iv. 2-(2-hydroxyethyl)-quinuclidine can be prepared by the application of any process for the homologation of an amino alcohol

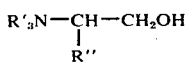

to

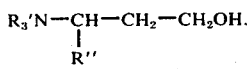

The following method, in particular, can be used.

a. Conversion of 2-hydroxymethyl-quinuclidine into a reactive ester thereof (such as a halide or a sulphonic ester) by the use of any known method for replacing a hydroxyl group by a halogen or a reactive ester group; in particular 2-chloromethyl-quinuclidine can be prepared as described by Prelog and coll., *Annalen*, 545 (1940), 259.

b. Reaction of the derivative obtained with an alkali metal cyanide in an inert solvent at a temperature of from 80° to 100° C depending on the nature of the ester and of the solvent. 2-Chloromethyl-quinuclidine can, for example, be reacted with sodium cyanide in dimethyl sulphoxide at 80° C.

c. Conversion of the nitrile obtained into a methyl or ethyl ester by the use of any known process for converting a nitrile R-CN into an ester R—COOR'. The nitrile can, for example, be saponified to form the corresponding acid by the action of a concentrated mineral acid at room temperature and the acid obtained can then be esterified to form the methyl or ethyl ester, particularly by reaction with methanol or ethanol saturated with anhydrous hydrogen chloride, at room temperature.

d. Reduction of the ester thus obtained to the alcohol, for example by means of lithium aluminium hydride in the presence of an inert solvent, such as ethyl ether.

The compounds of formula I obtained by the above-described processes can be purified by physical methods (such as distillation, crystallisation and chromatography) or by chemical methods (such as the formation of salts followed by the regeneration of the base by treatment of the salt in an alkaline medium).

The compounds of formula I can be converted into their addition salts by treatment with inorganic or organic acid in the presence of a suitable solvent (for example, alcohols, ethers, ketones or chlorinated solvents) and into their quaternary ammonium salts by treatment with inorganic or organic esters, if desired in the presence of a solvent, at room temperature or with gentle heating.

The following examples are given by way of illustration only:

EXAMPLE 1

10-(2-Quinuclidinyl-methyl)-phenothiazine

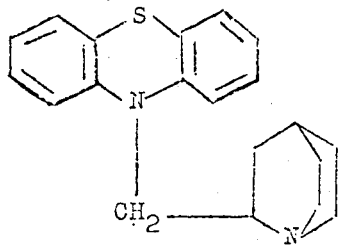

57.6 g of phenothiazine were added, all at once, to a suspension of 11.5 g of sodium amide in 200 ml of anhydrous xylene. The mixture was agitated and heated to reflux. When evolution of ammonia ceased (4 hours), 25 g of 2-chloromethyl-quinuclidine hydrochloride were introduced portionwise over a period of 50 minutes and reflux was continued for 24 hours. After cooling to room temperature, 150 ml of distilled water and 100 ml of ethyl acetate were added to the reaction mixture. The aqueous solution was decanted and then extracted three times with a total of 300 ml of ethyl acetate. The combined organic extracts were filtered through paper and extracted five times with a total of 750 ml of an acid 2N aqueous solution of methane-sulphuric acid. The combined acid extracts were treated with 5 g of animal charcoal, filtered and rendered alkaline on an ice bath with 130 ml of 10N aqueous caustic soda. The oil which was salted out was extracted three times with a total of 600 ml of ethyl acetate. The combined extracts were washed three times with a total of 750 ml of distilled water until they were neutral, dried over anhydrous magnesium sulphate and evaporated. The residue (19.3 g) was dissolved in 300 ml of a 50:50 mixture of cyclohexane and benzene. The solution obtained was chromatographed on a column of inert alumina. After elution first with benzene and then with ethyl acetate, the eluates were combined and evaporated. 14.6 g of crystallised product were obtained.

A 13.9 g portion of this product was dissolved in 70 ml of boiling absolute ethanol and a hot solution of 5 g of fumaric acid in 50 ml of absolute ethanol was added to the solution obtained. After cooling for 15 hours at 3° C, the crystals obtained were separated, washed three times by being suspended in iced ethanol, and then dried at room temperature under reduced pressure. 14 g of 10-(2-quinuclidinyl-methyl)-phenothiazine fumarate, m.p. 245° C., were obtained. The pure base, m.p. 168° C, was obtained by decomposition of the fumarate in an alkaline medium.

The 2-chloromethyl-quinuclidine starting material for this process can be prepared as described by Prelog and coll., *Annalen*, 545 (1940), 259.

EXAMPLE 2

10-(3-Quinuclidinyl-methyl)-phenothiazine

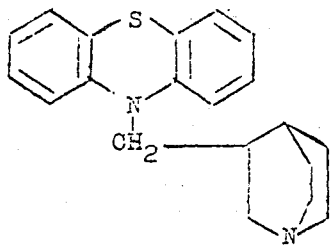

30 g of phenothiazine were added, all at once, to a suspension of 6 g of sodium amide in 240 ml of anhydrous xylene. The mixture was agitated and heated to reflux. When evolution of ammonia ceased (5 hours), 15 g of 3-chloromethyl-quinuclidine hydrochloride were added portionwise over a period of 50 minutes and reflux was then maintained for 22 hours. After cooling to room temperature, 250 ml of distilled water and 250 ml of ethyl acetate were added to the reaction mixture. The aqueous phase was decanted and extracted twice with a total of 250 ml of methyl acetate. The combined organic extracts were extracted three times with a total of 750 ml of a 10% aqueous solution of tartaric acid. The combined acid solutions were treated with 5 g of animal charcoal, filtered and rendered alkaline on an ice bath with 96 ml of ION aqueous caustic soda. The oil which separated was extracted three times with a total of 1500 ml of ethyl acetate. The combined organic extracts were washed to neutrality by washing twice with a total of 1 l. of distilled water, dried over anhydrous magnesium sulphate and evaporated under reduced pressure on a water bath at 45° C. 17 g of oil were obtained which was purified by chromatography on an inert alumina column as in Example 1. 13.3 g of crystallised product were obtained. 10-(3-Quinuclidinyl-methyl)-phenothiazine having m.p. 130° – 131° C was obtained by recrystallisation in boiling acetonitrile.

The 3-chloromethyl-quinuclidine hydrochloride used as starting material in this process can be obtained as described by Grob and coll., *Helv. Chim. Acta*, 37 (1954), 1689.

EXAMPLE 3

10-(2-Quinuclidinyl-ethyl)-phenothiazine

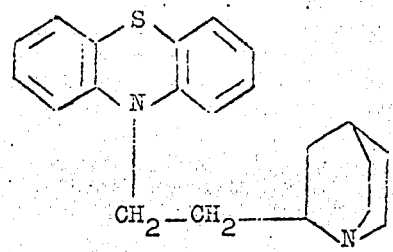

24.7 g of phenothiazine were added, all at once, to a suspension of 5 g of sodium amide in 1350 ml of anhydrous xylene. The mixture was agitated and heated to reflux. After evolution of ammonia ceased, 13 g of 2-chloroethyl-quinuclidine hydrochloride were added portionwise over a period of 1 hour and reflux was then continued for 15 hours. After cooling to room temperature, 25 ml of distilled water were added to the reaction mixture. The aqueous solution was decanted and extracted three times with a total of 750 ml of ethyl acetate. The combined organic extracts were treated with 3 g of animal charcoal, filtered, and then extracted three times with a total of 900 ml of a 10% aqueous solution of tartaric acid. The combined acid extracts were treated with 3 g of animal charcoal, filtered and rendered alkaline on an ice bath with 150 ml of ION aqueous caustic soda. The oil which separated was extracted three times with a total of 1500 ml of ethyl acetate. The combined organic extracts were washed to neutrality with 1 l. of distilled water, dried over anhydrous magnesium sulphate and then evaporated under reduced pressure on a water bath at 45° C. 19 g of oil were obtained which were purified by chromatography on an inert alumina column as in Example 1.

A 10.4 g portion of the purified product was dissolved in a mixture of 10 ml of absolute ethanol and 25 ml of acetone; to the solution obtained there was added a boiling solution of 2.8 g of oxalic acid in 10 ml of acetone. After cooling for 4 hours at 3° C, the crystals obtained were separated, washed twice with a total of 50 ml of acetone, and dried at 40° C under reduced pressure (4 mm.Hg). 11 g of 10-(2-quinuclidinylethyl)-phenothiazine oxalate, m.p. 158° C, were obtained.

The 2-chloroethyl-quinuclidine hydrochloride used as starting material to this process, was prepared as follows:

a. 56.8 g of 2-chloromethyl-quinuclidine hydrochloride (prepared as described by Prelog and coll., *Annalen*, 545 (1940), 259) were decomposed in alkaline medium to give 38.3 g of 2-chloromethyl-quinuclidine. The oily base was stored over phosphoric anhydride.

b. 34.8 g of 2-chloromethyl-quinuclidine were reacted with sodium cyanide in dimethyl sulphoxide at 80° C for 28 hours, and the product obtained was isolated in the form of its hydrochloride to give 21 g of 2-cyanomethylquinuclidine hydrochloride, m.p. 250° C.

c. 20.8 g of 2-cyanomethyl-quinuclidine hydrochloride were hydrolysed with 12N hydrochloric acid at room temperature for 48 hours. 28 g of 2-carboxymethyl-quinuclidine hydrochloride, m.p. 234° C., were obtained.

d. 28 g of 2-carboxymethyl-quinuclidine were esterified by treatment with a solution of anhydrous hydrogen chloride in absolute ethanol for 48 hours at room temperature. 25 g of 2-ethoxycarbonylmethyl-quinuclidine hydrochloride were obtained.

e. 25 g of 2-ethoxycarbonylmethyl-quinuclidine hydrochloride were decomposed in an alkaline medium to give 15.9 g of the oily, hydroscopic, base which was stored over phosphoric anhydride.

f. 15.9 g of 2-ethoxycarbonylmethyl-quinuclidine were reduced with lithium aluminium hydride in the presence of ether under reflux to give 12.3 g of 2-hydroxyethylquinuclidine, m.p. 62°–64° C.

g. A solution of 10 g of 2-hydroxyethyl-quinuclidine in 80 ml of anhydrous chloroform was cooled to 0° C and treated with anhydrous gaseous hydrogen chloride. 50 ml of thionyl chloride were then added to the solution and the reaction mixture was heated to reflux for 3 hours. The excess thionyl chloride and the chloroform were removed by evaporation under reduced pressure on a water bath at 50° C. The residue was purified by washing with anhydrous ether. The ethereal suspension was filtered and the crystals obtained were dried under reduced pressure at room temperature. 12 g of 2-chloroethyl-quinuclidine, m.p. 202° C, were obtained.

EXAMPLE 4

10-(3-Quinuclidinyl)-phenothiazine

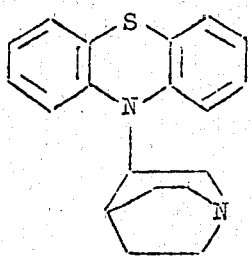

4 g of phenothiazine were added, all at once, to a suspension of 0.96 g of sodium amide in 35 ml of anhydrous toluene. The mixture was heated to reflux for 10 hours (i.e. until evolution of ammonia ceased). A solution of 5.3 g of 3-phenylsulphonyloxy-quinuclidine in 15 ml of anhydrous toluene was added drop by drop to the refluxing suspension of sodium phenothiazine over a period of 50 minutes and heating was then continued for 75 minutes. After cooling to room temperature, 75 ml of distilled water, 100 ml of ethyl acetate and 100 ml of ether were added to the reaction mixture. The aqueous phase was decanted and extracted three times with a total of 300 ml of ethyl acetate. The combined organic solutions were extracted five times with a total of 500 ml of a 1N aqueous solution of methanesulphonic acid. The combined acid solutions were rendered alkaline on an ice bath with 60 ml of 10N aqueous caustic soda and then saturated with sodium carbonate. The oil which separated was extracted three times with a total of 600 ml of ethyl acetate, the combined organic solutions were washed to neutrality by washing twice with a total of 200 ml of distilled water, dried over anhydrous magnesium sulphate and evaporated under reduced pressure on a water bath at 60° C. The oily residue (3g) was dissolved in 100 ml of cyclohexane and the solution was chromatographed on a column of inert alumina. The column was eluted first with cyclohexane and then with benzene and the combined eluates were evaporated under reduced pressure on a water bath at 60° C. 2.5 g of oil were obtained. A solution of 1 g of this product in 3 ml of cyclohexane was maintained for 2 hours at 3° C; the crystals obtained were separated, washed with 3 ml of cold cyclohexane and dried under reduced pressure at room temperature. 0.6 g of 10-(3-quinuclidinyl)-phenothiazine, m.p. 160°–162° C, was obtained.

The 3-phenylsulphonyloxy-quinuclidine used as starting material in this process can be prepared as described by Mikhlina and coll., *J. Gen. Chem. URSS*, 30, (1960), 2943.

EXAMPLE 5

2-Methoxy-10-(2-quinuclidinyl-methyl)-phenothiazine

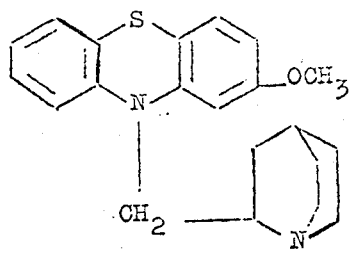

0.75 ml of hexamethylphosphotriamide and then 2.3 g of 2-methoxy-phenothiazine were added to a suspension of 0.48 g of sodium hydride in 20 ml of anhydrous toluene. The mixture was agitated and heated to reflux for 2 hours. 1 g of 2-chloromethyl-quinuclidine hydrochloride was added to the mixture and refluxing continued for 24 hours. After cooling to room temperature, 15 ml of distilled water were added to the reaction mixture, the toluene phase was decanted off and the aqueous phase was extracted twice with a total of 3.0 ml of ethyl acetate. The combined organic extracts were extracted three times with a total of 75 ml of an iced N aqueous methanesulphonic acid solution. The acid extracts were filtered and rendered alkaline on an ice bath with 8 ml of 10N aqueous sodium carbonate. The oil which separated was extracted three times with a total of 75 ml of ethyl acetate. The combined organic extracts were washed to neutrality by being washed three times with a total of 75 ml of distilled water, dried over anhydrous magnesium sulphate, and evaporated. The residue (0.5 g) was converted into the fumarate as in Example 1.

0.45 g of the neutral fumarate of 2-methoxy-10-(2-quinuclidinyl-methyl)-phenothiazine was thus obtained, m.p. 188° C.

EXAMPLE 6

2-Methoxy-10-(3-quinuclidinyl)-phenothiazine

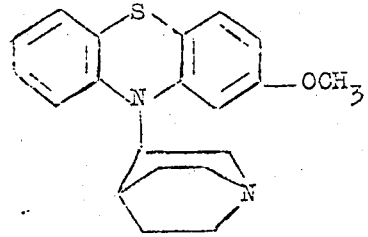

22.4 g of 2-methoxy-phenothiazine were added, all at once, to a suspension of 3.8 g of sodium amide in 250 ml of anhydrous xylene. The mixture was agitated and heated to reflux. When evolution of ammonia ceased (6 hours), heating was reduced in order to maintain the temperature of the reaction mixture at 100° C. A solution of 26 g of 3-phenylsulphonyloxy-quinuclidine in 50 ml of anhydrous toluene was added over a period of an hour and the mixture was maintained at 100°–110° C for 24 hours. After cooling to room temperature, 350 ml of distilled water and 350 ml of ether were added to the reaction mixture. The aqueous phase was decanted off and extracted twice with a total of 500 ml of ethyl acetate. The combined organic extracts were washed three times with a total of 450 ml of distilled water, filtered, and extracted three times with a total of 750 ml of an iced N aqueous methanesulphonic acid solution. The combined acid extracts were rendered alkaline on an ice bath with 100 ml of 10N aqueous sodium carbonate. The oil which separated was extracted three times with a total of 1500 ml of ethyl acetate. The combined organic extracts were washed three times with a total of 450 ml of distilled water, dried over magnesium sulphate, and evaporated. The residue (17.1 g) was purified by chromatography on an alumina column as in Example 4. 5 g of oil were obtained which was crystallised in ether. 2-Methoxy-10-(3-quinuclidinyl)-phenothiazine was thus obtained, m.p. 158° C.

EXAMPLE 7

2-Methoxy-10-(3-quinuclidinyl-methyl)-phenothiazine

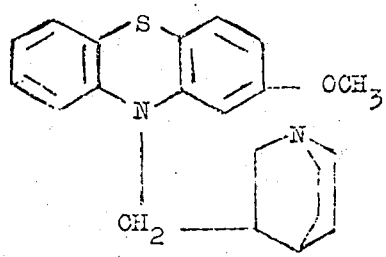

19.8 ml of a 50% suspension of sodium amide in xylene were added to a suspension of 68.3 g of 2-methoxyphenothiazine in 700 ml of anhydrous xylene.

The mixture was agitated and heated to reflux. After 4½ hours, 272 ml of an 8.5% solution of 3-chloromethyl-quinuclidine in xylene were added over a period of an hour and reflux was maintained for 16 hours. After cooling to room temperature, the reaction mixture was worked up as in Example 2. After recrystallisation of the crude product in a mixture of ether and isopropyl oxide, 2-methoxy-10-(3-quinuclidinylmethyl)-phenothiazine, m.p. 135°–136° C, was obtained.

EXAMPLE 8

2-Chloro-10-(3-quinuclidinyl-methyl)-phenothiazine

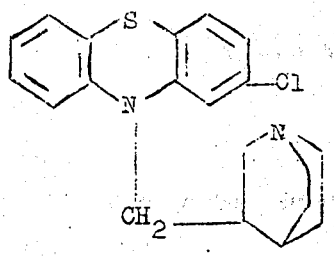

3 ml of a 35% suspension of sodium amide in xylene were added to a suspension of 7 g of 2-chloro-phenothiazine in 100 ml of anhydrous xylene. The mixture was agitated and heated to reflux. When evolution of ammonia ceased (20 hours), a solution of 0.35 g of potassium iodide in 2.3 ml of dimethylformamide was added to the reaction mixture all at once and 34 ml of a 7% solution of 3-chloromethyl-quinuclidine in xylene were then added over a period of an hour. Refluxing of the reaction mixture was continued for 32 hours. After cooling, the reaction mixture was worked up as in Example 2. After recrystallisation of the crude product in in isopropyl oxide, 2-chloro-10-(3-quinuclidinyl-methyl)-phenothiazine, m.p. 122° C, was obtained.

EXAMPLE 9

2-trifluoromethyl-10-(3-quinuclidinyl-methyl)-phenothiazine

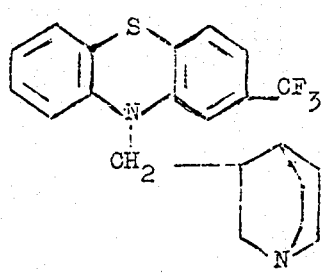

0.9 ml of a 65% suspension of sodium amide in xylene and then 25 ml of hexamethylphosphotriamide were added to a suspension of 5.3 g of 2-trifluoromethyl-phenothiazine in 25 ml of xylene. The mixture was agitated and heated to reflux. When the evolution of ammonia ceased (2 hours), 16.3 ml of a 9.8% solution of 3-chloromethyl-quinuclidine in xylene were added to the reaction mixture over a period of 30 minutes and refluxing was continued for 18 hours. After cooling, the xylene was evaporated off under reduced pressure and the residual solution was poured into 250 ml of distilled water. The precipitate obtained was separated on Clarcel filter medium, washed with 50 ml of distilled water, and then suspended in 100 ml of ethyl acetate. The insoluble portion was filtered off and the filtrate was washed with 30 ml of distilled water, and then extracted three times with a total of 150 ml of N.aqueous acetic acid. The combined acid extracts were rendered alkaline on an ice bath with 25 ml of 10N aqueous sodium carbonate and the oil which separated was extracted twice with a total of 200 ml of ethyl acetate. The combined organic extracts were dried over magnesium sulphate and evaporated. The residue was recrystallised in acetonitrile; 2-trifluoromethyl-10-(3-quinuclidinyl-methyl)-phenothiazine, m.p. 150° C, was obtained.

EXAMPLE 10

2-Chloro-10-(3-quinuclidinyl)-phenothiazine

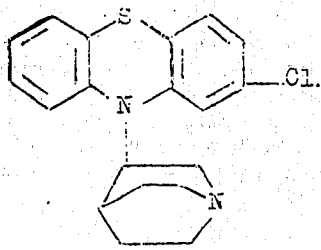

6 ml of dimethylformamide and then 5 ml of a 50% suspension of sodium amide in xylene were added to a suspension of 18.8 g of 2-chloro-phenothiazine in 200 ml of anhydrous xylene. The mixture was agitated and heated to reflux.

When evolution of ammonia ceased (5 hours), 0.3 g of potassium iodide were added to the mixture and then a solution of 10.8 g of 3-phenylsulphonyloxy-quinuclidine in 40 ml of anhydrous xylene was added over a period of 50 minutes and refluxing was continued for 16 hours. After cooling to room temperature, the reaction mixture was worked up as in Example 6. 2-Chloro-10-(3-quinuclidinyl)-phenothiazine, m.p. 165° C, was obtained.

Animal tests with the compounds according to the invention have shown that the latter have valuable pharmacological activities, particularly in the following areas:

i. antihistaminic: activity equal in intensity to that of the most active known antihistaminics, coupled with greater duration of action and absence of sedative activity;

ii. antidepressor: activity equal to that of imipramine in the animal tests usually used (inhibition of the central effects of reserpine, potentiation of the stereotype movements due to amphetamine, potentiation of adrenalinic hypertension, etc.);

iii. psycholeptic: activity as shown by conventional tests for tranquillising or neuroleptic activity which varies according to the compound.

In addition, the novel compounds have more or less marked central and peripheral cholinolytic activities.

Suitable dosages of the new compounds when used therapeutically will depend on the desired effect, the mode of administration and the duration of treatment: in general suitable adult dosages are from 10 to 200 mg of the active compound per day for oral administration and from 1 to 50 mg of the active compound per day for parenteral administration.

The compounds can be used for this purpose in the form of the free base or in the form of a physiologically acceptable acid addition or quaternary ammonium salt, that is a salt which is non-toxic at the doses used. Suitable physiologically acceptable addition salts are those formed with inorganic acids, such as hydrochloric, hydrobromic, sulphuric and phosphoric acid, and those formed with organic acids, such as acetic, propionic, succinic, maleic, fumaric, tartaric, citric, oxalic, benzoic, anthranilic, salicylic, methanesulphonic and naphthoic acid, and the substitution derivatives of these acids.

Suitable physiologically acceptable quaternary ammonium salts include those derived from inorganic esters, such as methyl, ethyl, propyl, butyl, alkyl and benzyl chlorides, bromides, iodides, sulphates and benzenesulphonates, and the substitution derivatives of these esters.

In pharmaceutical compositions, the novel compounds may be associated with one or more of the following: diluents, coating agents, preservatives, wetting agents, lubricants, dissolution additives, colourants and perfumes; these materials should, of course, be physiologically acceptable and appropriate to the intended mode of administration.

For oral administration, the pharmaceutical composition may take the form of compressed tablets, dragees, powders, granules, capsules, emulsions, suspensions, solutions or syrups.

For parenteral administration, the pharmaceutical composition may take the form of aqueous or non-aqueous sterile solutions, suspensions or emulsions or even sterile powders suitable for dissolution at the time of use.

For rectal administration, the pharmaceutical composition is suitably in the form of suppositories and for topical applications, it is suitably in the form of solutions, emulsions, suspensions or ointments.

The following example of the formulation of a compressed tablet is given by way of illustration only:

| | |
|---|---|
| 10-(3-Quinuclidinyl-methyl)-phenothiazine | 25 mg |
| Mannitol | 92 mg |
| Maize starch | 20 mg |
| Stearic acid | 8 mg |
| Talc | 5 mg | to make a tablet weighing 150 mg.

We claim:
1. 10-(3-Quinuclidinyl-methyl)-phenothiazine.

* * * * *